US011488706B2

(12) United States Patent
Freese et al.

(10) Patent No.: US 11,488,706 B2
(45) Date of Patent: *Nov. 1, 2022

(54) PHYSICIAN QUALITY SCORING

(71) Applicant: Included Health, Inc., San Francisco, CA (US)

(72) Inventors: Nathaniel Freese, Oakland, CA (US); Evan Richardson, Menlo Park, CA (US); Owen Tripp, San Francisco, CA (US)

(73) Assignee: INCLUDED HEALTH, INC., San Francisco, CA (US)

( * ) Notice: Subject to any disclaimer, the term of this patent is extended or adjusted under 35 U.S.C. 154(b) by 147 days.

This patent is subject to a terminal disclaimer.

(21) Appl. No.: 16/885,203

(22) Filed: May 27, 2020

(65) Prior Publication Data

US 2021/0183503 A1 Jun. 17, 2021

Related U.S. Application Data

(63) Continuation of application No. 14/476,483, filed on Sep. 3, 2014, now Pat. No. 10,692,597.

(51) Int. Cl.
*G16H 40/20* (2018.01)
(52) U.S. Cl.
CPC ................ *G16H 40/20* (2018.01)
(58) Field of Classification Search
CPC ........ G06Q 50/22; G06Q 50/24; G06Q 40/08; G06Q 10/10; G06F 19/32
See application file for complete search history.

(56) References Cited

U.S. PATENT DOCUMENTS

| 2012/0116985 A1* | 5/2012 | Rastogi | ............... G06Q 30/018 705/347 |
| 2012/0284045 A1 | 11/2012 | Hicks et al. | |
| 2012/0296667 A1 | 11/2012 | Schoenberg | |
| 2015/0006261 A1* | 1/2015 | Gutman | ................. G16H 70/00 705/7.39 |
| 2015/0356248 A1 | 12/2015 | Kogan et al. | |

FOREIGN PATENT DOCUMENTS

WO     WO-9840126 A1 * 9/1998  ........... A61B 5/1036

OTHER PUBLICATIONS

Eric S Holmboe, Weifeng Weng, Gerald K Arnold, Sherrie H Kaplan, Sharon-Lise Normand, Sheldon Greenfield, Sarah Hood, and Rebecca S Lipner. "The Comprehensive Care Project: Measuring Physician Performance in Ambulatory Practice." Health Serv Res. Dec. 2010; 45(6 Pt 2): 1912-1933. (Year: 2010).*

* cited by examiner

*Primary Examiner* — Linh Giang Le
(74) *Attorney, Agent, or Firm* — Finnegan, Henderson, Farabow, Garrett & Dunner, LLP

(57) ABSTRACT

Aspects of the present invention relate to system and methods for assigning quality scores to one or more caregivers, such as physicians. In embodiments, a ranking or score may be based, at least in part, upon a combination of quality scores from one or more stages in a physician's academic training and clinic practice and based, at least in part, upon the quality of peers of that physician at various stages in the career progression of the physician. This information may be used to help a potential patient identify a physician for their care.

20 Claims, 12 Drawing Sheets

700

```
Calculate a first coefficient of determination where
physician's RP scores are assumed to be a linear     — 705
function of their MS score
              │
              ▼
Calculating a second coefficient of determination
where physicians' FP score are assumed to be a       — 710
linear function of their RP score
              │
              ▼
Use the first and second coefficients of             — 715
determination to obtain the correlation factor
              │
              ▼
Maximize the correlation factor across all physcians — 720
```

Determine a physician's training score based, at least in part, upon quality of the physician's peers — 1005

Determine a rating for the physician's practice location based, at least in part, upon quality of the physician's peers at the practice location — 1010

Assign the physician's overall quality score based, at least in part, upon the physician's training score and the rating for the physician's practice location — 1015

FIGURE 10

PHYSICIAN QUALITY SCORING

This application is a continuation of application Ser. No. 14/476,483 entitled "Physician Quality Scoring", filed Sep. 3, 2014, and which is incorporated herein by reference in its entirety.

BACKGROUND

Field of Invention

The present invention relates generally to data processing, and relates more particularly to system and methods for assessing and scoring a physician.

Description of the Related Art

Healthcare as an industry has become increasing more complex and costly. The number and type of healthcare providers available to patients is likewise vast. Added to this ever-increasingly expanding system is a significant absence of important information. Unlike most other industries, the healthcare industry provides very little information to help patients make informed decision when selecting a physician. Yet, the selection of a physician by a patient can have considerable—even critical—effects upon the patient's treatment and recovery.

Currently, most reviews or rankings of physicians, particularly those from patients, are based on non-quality-related factors, such as niceness of doctor, wait times, cleanliness of the waiting area, etc. Unfortunately, this information is of little or no value when trying to find the best quality doctor and can, in fact, be misleading and detrimental if the wrong metrics are taking for surrogates for quality.

Accordingly, what is needed are systems and methods to help gather data related to physicians and use that data to help assess the quality of a caregiver or set of caregivers.

BRIEF DESCRIPTION OF THE DRAWINGS

Reference will be made to embodiments of the invention, examples of which may be illustrated in the accompanying figures, in which like parts may be referred to by like or similar numerals. These figures are intended to be illustrative, not limiting. Although the invention is generally described in the context of these embodiments, it should be understood that it is not intended to limit the spirit and scope of the invention to these particular embodiments. These drawings shall in no way limit any changes in form and detail that may be made to the invention by one skilled in the art without departing from the spirit and scope of the invention.

FIG. 7 depicts a methodology for determining a correlation factor as part of the iteration process according to embodiments of the present invention

FIG. 10 depicts a method for determining a physician's overall quality score according to embodiments of the present invention.

DESCRIPTION OF THE PREFERRED EMBODIMENTS

Figure 1:
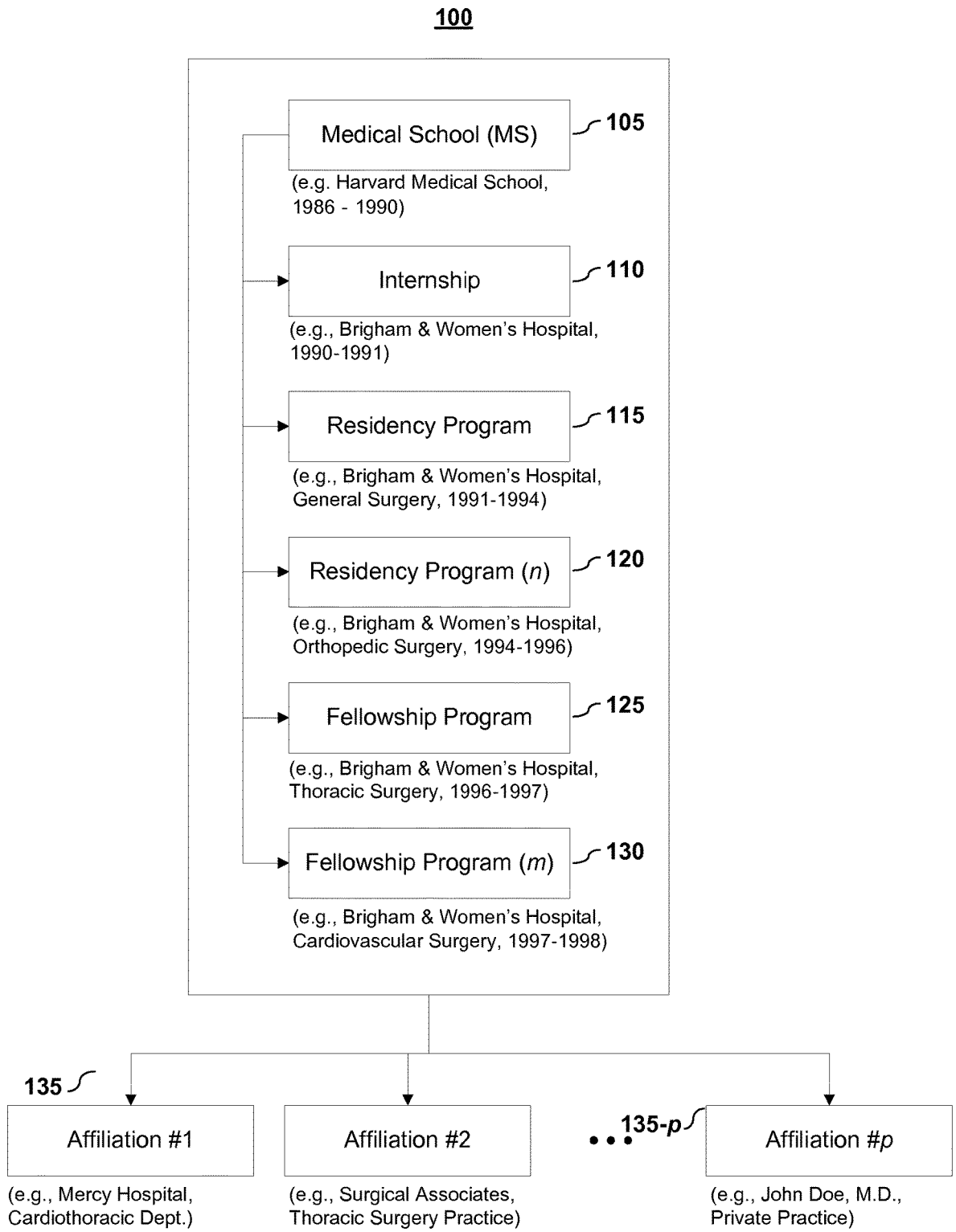
FIG. 1 depicts various stages in a physician's career that may be used in scoring a physician for a patient's specific needs according to embodiments of the present invention.

In the following description, for purposes of explanation, specific examples and details are set forth in order to provide an understanding of the invention. It will be apparent, however, to one skilled in the art that the invention may be practiced without these details. Well-known process steps may not be described in detail in order to avoid unnecessarily obscuring the present invention. Other applications are possible, such that the following examples should not be taken as limiting. Furthermore, one skilled in the art will recognize that aspects of the present invention, described herein, may be implemented in a variety of ways, including software, hardware, firmware, or combinations thereof.

Components, or modules, shown in block diagrams are illustrative of exemplary embodiments of the invention and are meant to avoid obscuring the invention. It shall also be understood that throughout this discussion that components may be described as separate functional units, which may comprise sub-units, but those skilled in the art will recognize that various components, or portions thereof, may be divided into separate components or may be integrated together, including integrated within a single system or component. It should be noted that functions or operations discussed herein may be implemented as components or modules.

Furthermore, connections between components within the figures are not intended to be limited to direct connections. Rather, data between these components may be modified, re-formatted, or otherwise changed by intermediary components (which may or may not be shown in the figure). Also, additional or fewer connections may be used. It shall also be noted that the terms "coupled" or "communicatively coupled" shall be understood to include direct connections, indirect connections through one or more intermediary devices, and wireless connections.

In the detailed description provided herein, references are made to the accompanying figures, which form a part of the description and in which are shown, by way of illustration, specific embodiments of the present invention. Although these embodiments are described in sufficient detail to enable one skilled in the art to practice the invention, it shall be understood that these examples are not limiting, such that other embodiments may be used, and changes may be made without departing from the spirit and scope of the invention.

Reference in the specification to "one embodiment," "preferred embodiment," "an embodiment," or "embodiments" means that a particular feature, structure, characteristic, or function described in connection with the embodiment is included in at least one embodiment of the invention and may be in more than one embodiment. Also, such phrases in various places in the specification are not necessarily all referring to the same embodiment or embodiments. It shall be noted that the use of the terms "set" and "group" in this patent document may include any number of elements. Furthermore, it shall be noted that methods or algorithms steps may not be limited to the specific order set forth herein; rather, one skilled in the art shall recognize, in some embodiments, that more or fewer steps may be performed, that certain steps may optionally be performed, and that steps may be performed in different orders and may include some steps being done concurrently.

It shall also be noted that although embodiments described herein may be within the context of physicians or other caregivers, the invention elements of the current patent document are not so limited. Accordingly, the invention elements may be applied or adapted for use in other industries and practices.

1. Overview of Physician Quality Scoring

FIG. 1 depicts various stages or factors 100 in a physician's training and career that may be used or considered when scoring a physician for quality or for a patient's specific needs according to embodiments of the present invention.

As shown in FIG. 1, one of the main stages in a physician's training is medical school 105. Factors that may be considered relate to medical school include, but are not limited to, the school (e.g., Harvard Medical School) and its ranking, the years attended, physician's personal Medical College Admission Test (MCAT) score and/or Grade Point Average (GPA), one or more grade point average (GPA) values and/or MCAT scores of the physician's entering class, one or more grade point average (GPA) values and/or MCAT scores of surrounding years' classes, and the like. For example, a medical student may have been accepted to Harvard Medical School and attended during the years 1986 through 1990. When gauging the quality of the training for that student, one or more metrics (e.g., GPA, MCAT score, etc.) related to that student's entering class may be used. Furthermore, one or more metrics of surrounding class years may also be used (e.g., that class year's GPA average, MCAT average, current or past GPA average in medical school, etc.).

It shall be noted that one or more various measures of GPA, MCAT, or other scores may be used. For example, the average (mean, median, and/or mode), top X percentile, range, etc. may be used.

The next stage shown in FIG. 1 is internship 110. In the United States, a medical intern generally refers to someone who has or is working to obtain a medical degree but is not allowed to practice medicine without direct supervision from someone who is fully licensed to practice medicine. Not all physicians participate in an internship program during the course of their training. However, a physician participation in a medical internship (or their lack of participation) may be considered when assessing the training quality of the physician.

Following medical school 105 or an internship 110, a medical school graduate will enroll in a residency program 115. Medical school involves more academic endeavors whereas residency programs focus more on the practical elements of the medical profession. Residency program may be general or directed to a specialty. For example, a person wanting to become a surgeon may become a surgical resident in a general surgical practice at a hospital.

Competition for residency programs can be fierce. Accordingly, the residency program to which a medical school graduate is admitted may be used as an indicator in the quality of training. Also, an assessment of the peers accepted to that residency program can also reflect upon the quality of the physician.

FIG. 1 illustrates that a physician may have participated in more than one residency 120. Each of these additional residency program or programs 120 may also be considered when determining a physician's training score.

The next stage shown in FIG. 1 is fellowship 125. A fellowship is typically an optional period of medical training or research focused on a certain specialty. A fellow may be a licensed physician who is capable of providing medical services to patients in the area in which they were trained but have not yet qualified for that certain specialty. After completing a fellowship, a physician may provide medical services in the fellowship specialty without direct supervision of another physician. For example, as shown in FIG. 1, the physician may have done a residency in general surgery at Brigham & Women's Hospital, but now desires to specialize in thoracic surgery. To obtain the specialized training, the physician may participate in a thoracic surgery fellowship. In some instances, the fellowship may be heavily research based in which much of the fellow's time is spent in lab work or clinic trials.

Like residency, a physician may have participated in more than one fellowship program 130. Each of these additional fellowship program or programs 130 may also be considered when determining a physician's training score.

After formal medical training, a physician may have one or more affiliations. These affiliations represent practices at which the physician may work or may have privileges. The quality of these organizations (e.g., Mercy Hospital) may be considered when scoring a physician's training quality score. Also, the quality of the physicians at the organizations may also be factored into the scoring. For example, the quality of doctors in the Surgical Associates group in Affiliation #2 shown in FIG. 1 may be considered when scoring the physician. If the Surgical Associates group comprises physicians with very good credentials (medical school, internships, residency programs, fellowship programs, other affiliates, etc.), this can help increase the score for the physician of interest.

It shall be noted that one or more additional scoring factors may be considered when scoring a physician. These additional scoring factors may include, but are not limited to:

(1) Publication Track Record. A physician's publications may be useful in scoring a physician. When considering publications, one or more of several elements may be considered, including but not limited to:
  (a) Subject matter covered in the publications;
  (b) Number of article citations;
  (c) Quality or scoring of co-authors;
  (d) Frequency of co-authoring over time and author number (e.g., first or last author); and
  (e) Trend(s) of publication volume and quality (e.g., impact factor) over time.

(2) Physician Referrals. Physician referral may also be useful in scoring a physician. When considering physician referrals, one or more of several elements may be considered, including by not limited to:
- (a) Quality and/or specialty of physicians who refer patients to the physician;
- (b) Quality and/or specialty of physicians to whom the physician refers patients to;
- (c) Frequency of inbound and outbound referrals; and
- (d) Concentration of inbound and outbound referrals.

(3) Volumes Data.
- (a) Surgical procedures;
- (b) Prescriptions;
- (c) Tests;
- (d) Diagnoses; and
- (e) etc.

(4) Outcomes metrics.
- (a) Survival rates;
- (b) Complications rates;
- (c) Readmissions rates; and
- (d) etc.

(5) Honors & Awards. (e.g., Chief Resident, Alpha Omega Alpha, F.A.S.C.O., etc.)

(6) Professional Organization Memberships.

(7) Positions Held. (e.g., Dept. Chair, Board Examiner, Professor, etc.)

(8) Years of Experience.

(9) Wait Time to Soonest Appointment.

(10) Etc.

2. Mapping Residency & Fellowship Programs

Figure 2:
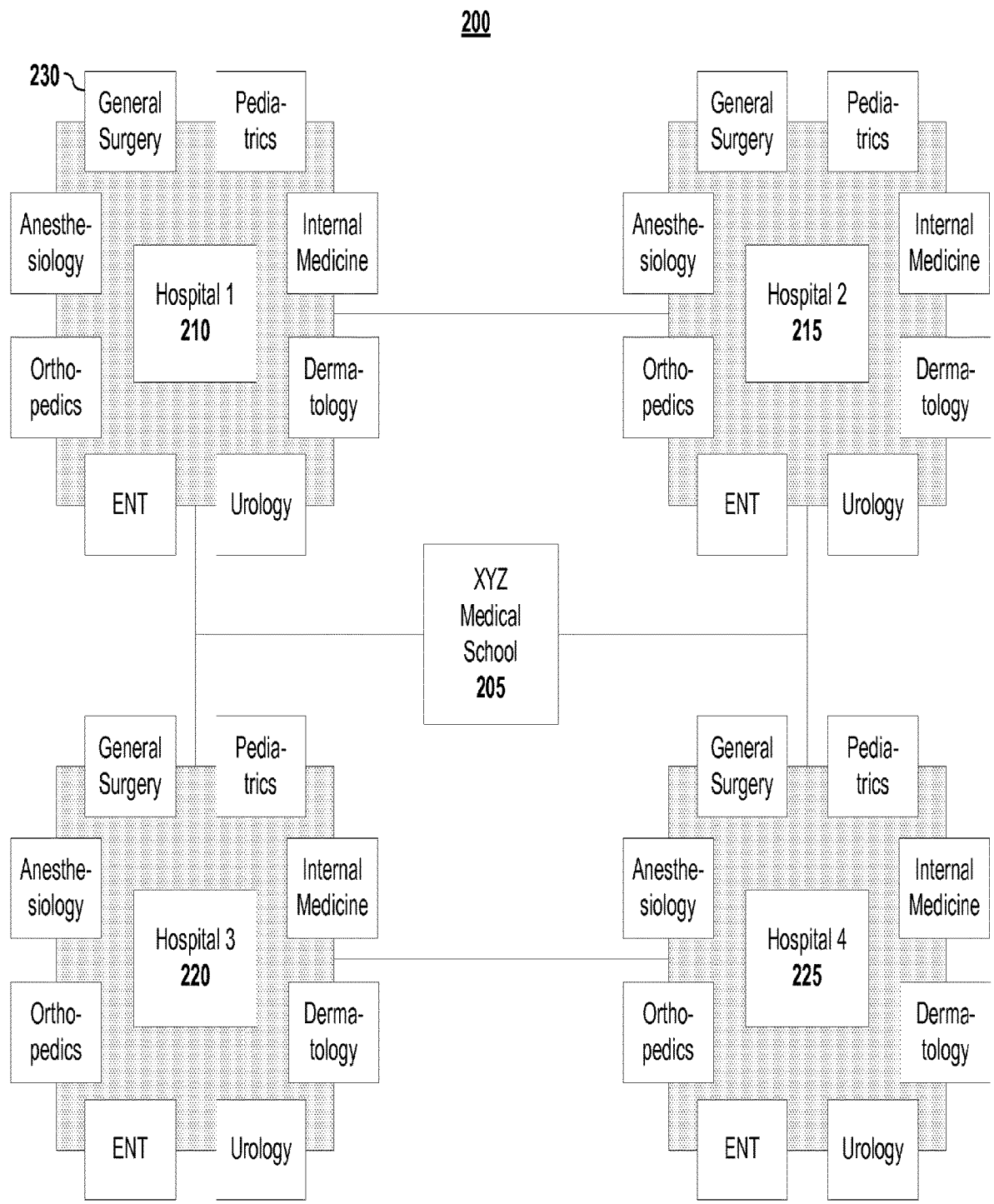
FIG. 2 depicts relationships between medical schools, hospitals, and specialty programs for which residency and fellowship programs may be offered according to embodiments of the present invention.

FIG. 2 depicts relationships between medical schools, hospitals, and specialty programs for which residency and fellowship programs may be offered according to embodiments of the present invention. As shown in FIG. 2, most hospitals offer residency and fellowship programs for numerous specialties (e.g., general surgery, pediatrics, dermatology, internal medicine, etc.). These programs may or may not be affiliated with a medical school. FIG. 2 depicts that the four hospitals (Hospital 1 210—Hospital 4 225) are affiliated with XYZ Medical School 205. In embodiments, the affiliations may be used in assessing quality of a program.

In embodiments, a residency or fellowship program quality may be assessed by the physicians attending a specific program and related programs. For example, the quality of the General Surgery residency at Hospital 230 is impacted by the residents who complete this program, as well as those who complete other Hospital 230 residencies and other XYZ Medical School-affiliated residencies. In embodiments, the weight of these relationships may vary by specialty. For example, General Surgery and Orthopedic Surgery residents may have a disproportionate impact on each other's program scores due to similarities in these programs. In embodiments, other institutional factors, such as resources and recognition, may also be considered.

3. Rating Medical School

In embodiments, quality of a physician's medical school (MS) may be assessed based on attributes of their peers, weighted by the proximity of those peers. An academic metric, such as average MCAT score and/or GPA score of an incoming class may be used. Attributes of previous and/or subsequent classes are also considered, but may be assigned a lower weight. Institutional factors, such as NIH funding, may also be considered.

Figure 3:
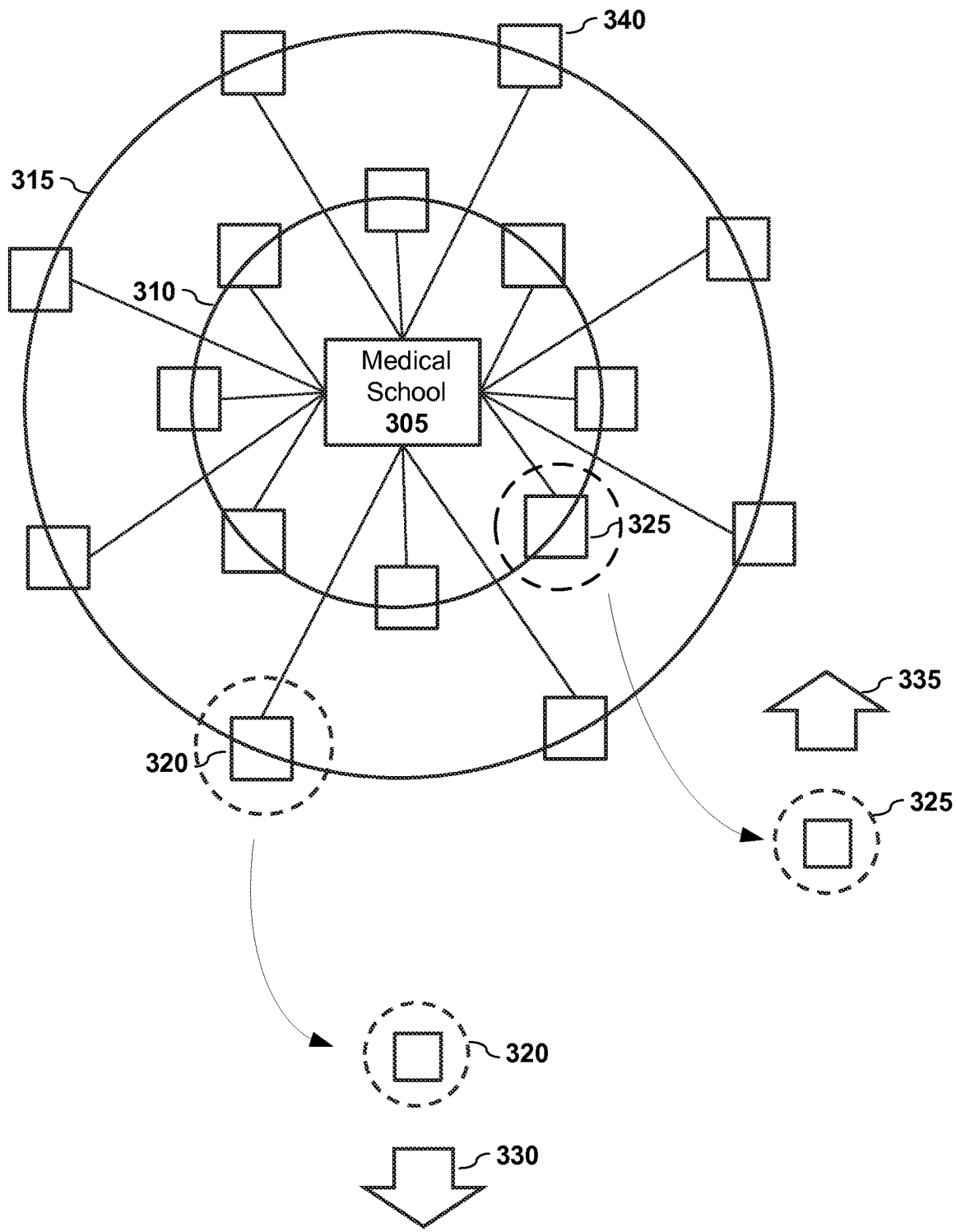
FIG. 3 graphically depicts the relationships between peers and medical school rating according to embodiments of the present invention.

FIG. 3 graphically depicts the relationships between peers and medical school rating according to embodiments of the present invention. In embodiments, a medical school 305 of a physician may be represented as having a set of one or more peers (e.g., box 340 may represent a single peer or a group of peers). In embodiments, each peer set may be weighted by proximity to the physician of interest. The proximity *nexus* may be based upon one or more factors such as time or area of study. Given that most medical students at the same school have the same or vary similar course of study, a proximity factor may be based upon time (e.g., class year).

FIG. 3 graphically depicts these temporal connections via the circles or rings. For example, the inner circle 310 represents peer groups that were the same entering class year as the physician of interest, and the outer circle 315 represents peer groups that were one year away (e.g., one year prior, one year after, or both) from the entering class year as the physician of interest. Only two groups 310 and 315 are depicted for sake of explanation, but it shall be noted that more or fewer groups may be considered and that the temporal categories may represent various ranges of time.

As shown in FIG. 3, in embodiments, physicians who attended the same medical school long before or long after the selected physician (e.g., peer set 320) may have a lower proximity weighting as depicted by the weighting factor 330. Conversely, in embodiments, physicians (e.g., physician set 325) who attended the same medical school within a shorter time period (e.g., the same year or within a few years) of the selected physician may be given more weight as graphically illustrated by the weighting factor 335.

As mentioned previously, in embodiments, the medical school score may be determined based, at least in part, upon one or more academic metrics and residency program scores of at least some of the physician's medical school peers. In embodiments, the medical school score may also be a function of one or more institutional factors.

For example, in embodiments, the Medical School (MS) score may be determined as follows:

$$MS = \text{Physician's Medical School Score}$$
$$= f(MS_{source}, MS_{place}, \text{Institutional Factor(s)})$$
$$\text{e.g.,} = \lambda * MS_{source} + \eta * MS_{place} + \theta * NIH \text{ Funding}$$

where:

$$MS_{source} = f(MCAT, GPA)$$

$$\text{e.g.,} = \alpha * MCAT_{median} + \delta * GPA_{median}$$

$$MS_{place} = f(\text{Peers' Residency Program, Specialty, Time Attended})$$

$$\text{e.g.,} = \frac{1}{n}\sum_{i=0}^{n} D_i(\alpha RP, \mu S, \delta T)$$

where:
- n=Number of physicians who attended the medical school
- $D_i(\ )$=Individual physician's score
- RP=A physician's residency
- S=Specialty (e.g., General Surgery)
- T=Time Attended (e.g., 1993)

$$\text{e.g.,} = \frac{1}{n}\sum_{i=0}^{n} RP_i$$

for all peers with the same specialty, S, who attended the program within X years of the physician where:

n=Number of physicians who attended the medical school $RP_i$=A physician's Residency Program score 4. Rating Residency Program In embodiments, quality of a physician's residency program (RP) may be assessed based on attributes of their peers. For example, in embodiments, one or more of the following factors may be considered when determining the residency program quality: (1) the quality of medical schools previously attended by these peers; (2) the quality of fellowship programs subsequently attended; and (3) a peer's "proximity" to the physician of interest (e.g., closeness in time to when they were in the residency, whether they attended a different program at the same institution or a similar program at an affiliated institution, etc.).

Figure 4:
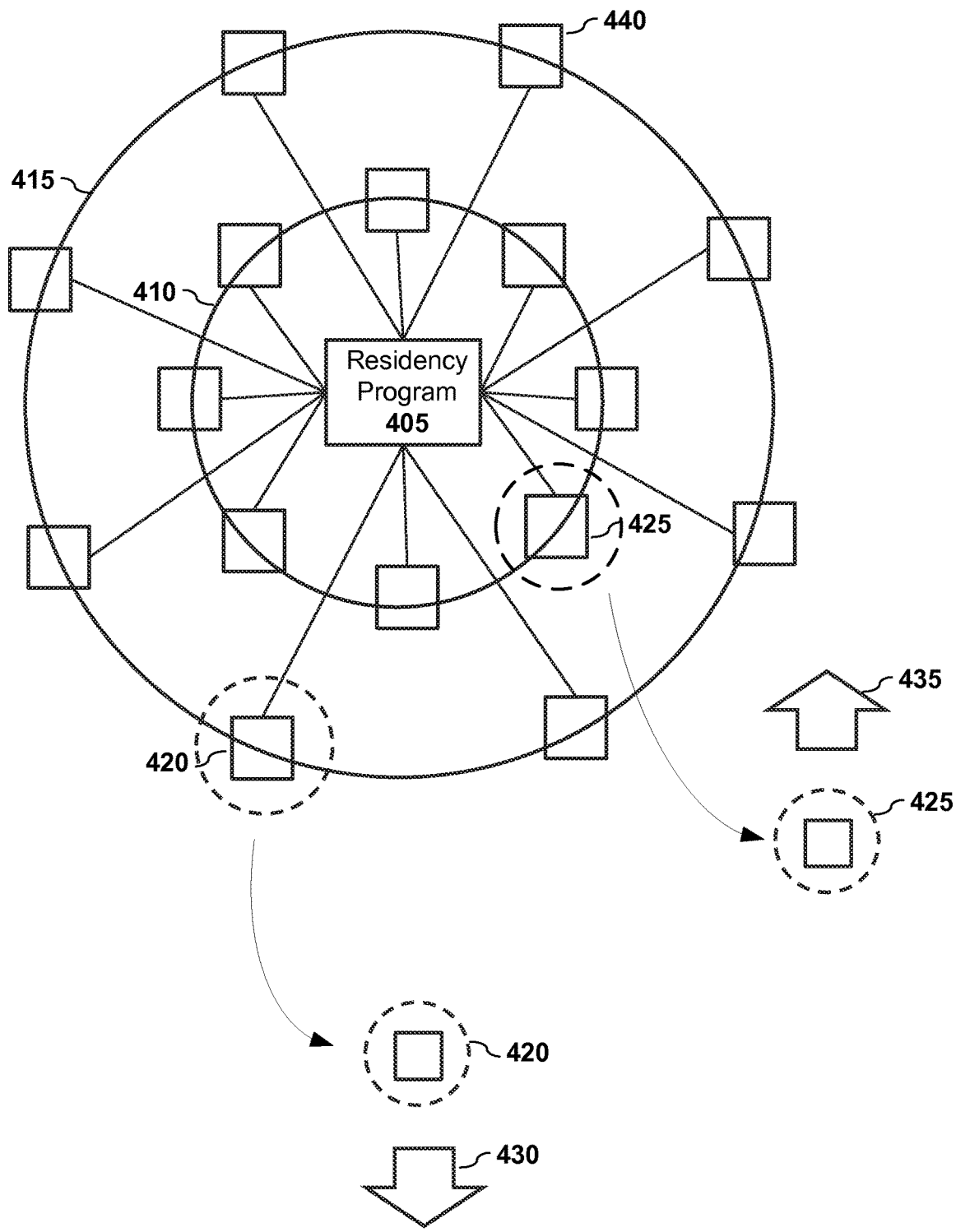
FIG. 4 graphically depicts the relationships between peers and residency program rating according to embodiments of the present invention.

FIG. 4 graphically depicts the relationships between peers and residency program rating according to embodiments of the present invention. In embodiments, a residency program 405 of a physician may be represented as having a set of one or more peers (e.g., box 440 may represent a single peer or a group of peers). In embodiments, each peer set may be weighted by proximity to the physician of interest. The proximity nexus may be based upon one or more factors such as time, institution, residency specialty, etc.

FIG. 4 graphically depicts these connections via the circles or rings. For example, the inner circle 410 represents physicians who completed the same residency within a few years of the selected physician. And, in embodiments, the outer circle 415 represents peer groups that were in the same residency program but at a different time period, that were in a different program at the same institution, or that were in a similar program at an affiliated institution. Only two groups 410 and 415 are depicted for sake of explanation, but it shall be noted that more or fewer groups may be considered and that the categories may represent various factors or various combinations of factors as suggested above.

As shown in FIG. 4, in embodiments, physicians who have a close *nexus* to the selected physician (e.g., peer set 425) may have a higher proximity weighting as depicted by the weighting factor 435. Conversely, in embodiments, physicians (e.g., physician set 420) who do not have as close a nexus to the selected physician may be given less weight as graphically illustrated by the weighting factor 430.

In embodiments, a residency program score for the physician may be determined based, at least in part, upon one or more incoming peer attributes (e.g., medical school scores) and one or more outgoing peer attributes (e.g., fellowship program scores) of at least some of the physician's peers in one or more residency programs. In embodiments, the residency program score may also be a function of one or more institutional factors.

For example, in embodiments, the Residency Program (RP) score may be determined as follows:

$$RP = \text{Physician's Residency Program Score}$$
$$= f(RP_{source}, RP_{place}, \text{Institutional Factor}(s))$$
$$\text{e.g.,} = \lambda * RP_{source} + \eta * RP_{place} + \theta * NIH \text{ Funding}$$

where:

$$RP_{source} = f(\text{Peer's Medical School, Time Attended})$$

$$\text{e.g.,} = \frac{1}{n}\sum_{i=0}^{n} C_i(\alpha MS, \mu S, \delta T)$$

where:

n=Number of physicians who attended the residency program $C_i(\ )$=Individual physician's score MS=A physician's medical school S=Specialty (e.g., General Surgery)

T=Time Attended (e.g., 1993)

$$\text{e.g.,} = \frac{1}{n}\sum_{i=0}^{n} MS_i$$

for all peers with the same specialty, S, who attended the program within X years of the physician where:

n=Number of physicians who attended the residency program $MS_i$=A physician's Medical School score $$RP_{place} = f(\text{Peers' Fellowship Program, Time Attended})$$

$$\text{e.g.,} = \frac{1}{n}\sum_{i=0}^{n} D_i(\alpha FP, \mu S, \delta T)$$

where:

n=Number of physicians who attended the residency program $D_i(\ )$=Individual physician's score FP=Fellowship Program (e.g., Steadman Hawkins)

S=Specialty (e.g., General Surgery)

T=Time Attended (e.g., 1993)

$$\text{e.g.,} = \frac{1}{n}\sum_{i=0}^{n} FP_i$$

for all peers with the same specialty, S, who attended the program within X years of the physician where:

n=Number of physicians who attended the residency program $FP_i$=A physician's Fellowship Placement score 5. Rating Fellowship Program In embodiments, quality of a physician's fellowship program (FP) may be assessed based on attributes of their peers. For example, in embodiments, one or more of the following factors may be considered when determining the fellowship program quality: (1) the quality of residency programs previously attended by these peers; (2) the quality of the institutions where they subsequently practice; and (3) a peer's "proximity" to the physician of interest (e.g., closeness in time to when they were in the fellowship, whether they attended a different program at the same institution or a similar program at an affiliated institution, etc.). In embodiments, institutional factors, such as publication track record, may also be considered.

Figure 5:
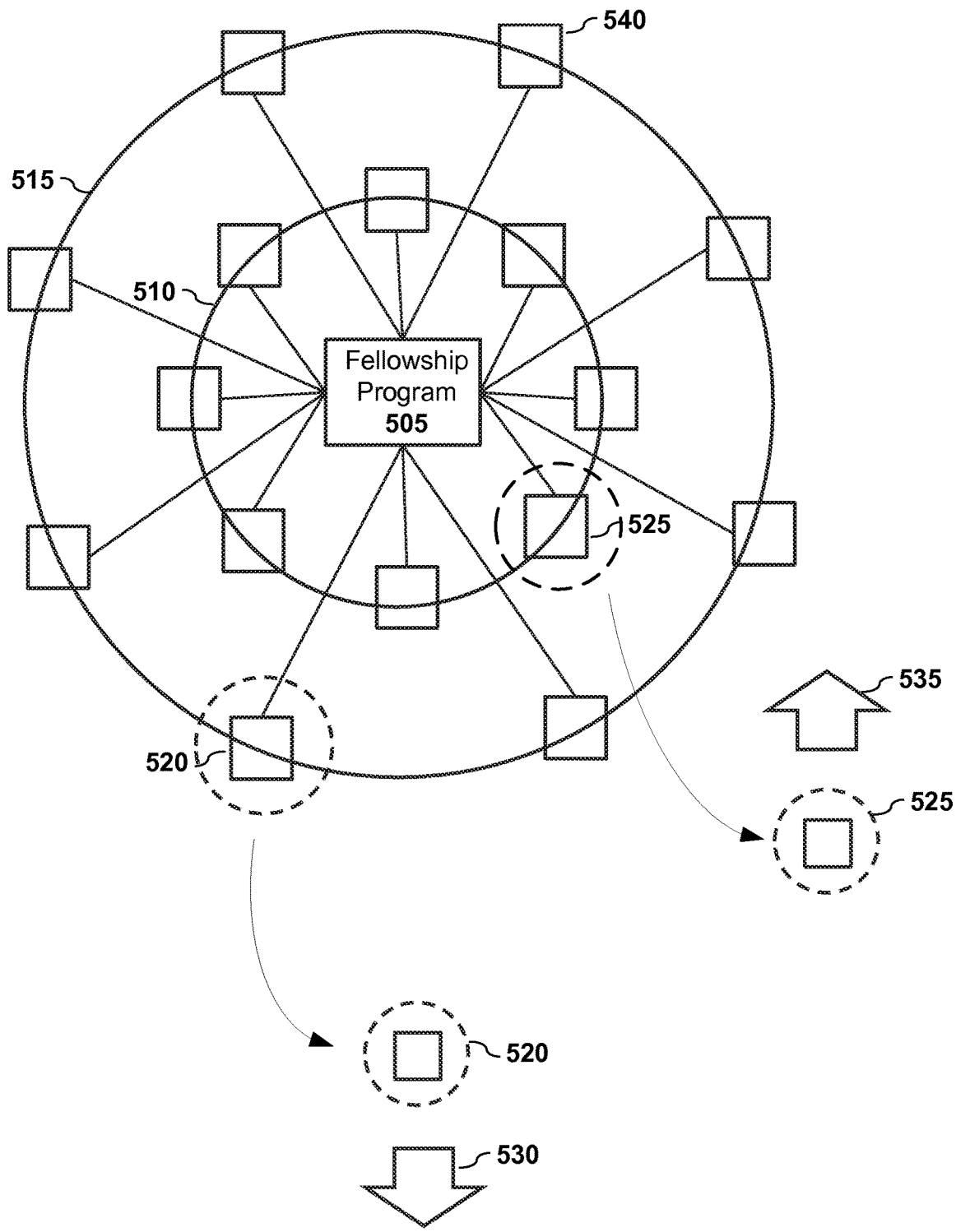
FIG. 5 graphically depicts the relationships between peers and fellowship program rating according to embodiments of the present invention.

FIG. 5 graphically depicts the relationships between peers and fellowship program rating according to embodiments of the present invention. In embodiments, a fellowship program 505 of a physician may be represented as having a set of one or more peers (e.g., box 540 may represent a single peer or a group of peers). In embodiments, each peer set may be weighted by proximity to the physician of interest. The proximity *nexus* may be based upon one or more factors such as time, institution, fellowship specialty, etc.

FIG. 5 graphically depicts these connections via the circles or rings. For example, the inner circle 510 represents physicians who completed the same fellowship within a few years of the selected physician. And, in embodiments, the outer circle 515 represents peer groups that were in the same fellowship program but at a different time period, that were in a different program at the same institution, or that were in a similar program at an affiliated institution. Only two groups 510 and 515 are depicted for sake of explanation, but it shall be noted that more or fewer groups may be considered and that the categories may represent various factors or various combinations of factors as suggested above.

As shown in FIG. 5, in embodiments, physicians who have a close *nexus* to the selected physician (e.g., peer set 525) may have a higher proximity weighting as depicted by the weighting factor 535. Conversely, in embodiments, physicians (e.g., physician set 520) who do not have as close a *nexus* to the selected physician may be given less weight as graphically illustrated by the weighting factor 530.

In embodiments, a fellowship program score for the physician may be determined based, at least in part, upon one or more incoming peer attributes (e.g., residency program scores) and one or more outgoing peer attributes (e.g., practice groups/locations scores) of at least some of the physician's peers in one or more fellowship programs. In embodiments, the fellowship program score may also be a function of one or more institutional factors.

Figure 6:
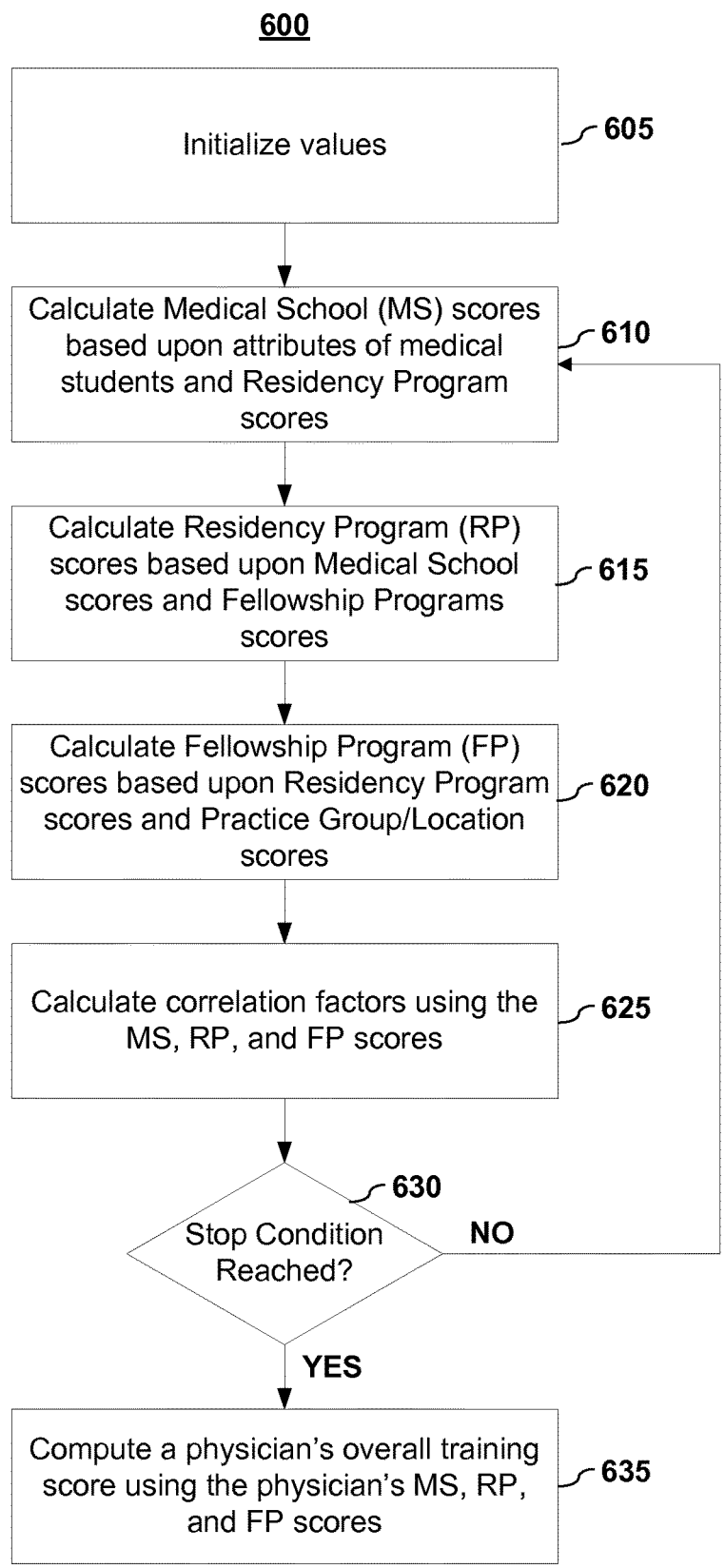
FIG. 6 depicts a methodology for assigning an overall training score to a physician according to embodiments of the present invention.

For example, in embodiments, the Fellowship Program (FP) score may be determined as follows:

$$FP = \text{Physician's Fellowship Program Score}$$
$$= f(FP_{source}, FP_{place}, \text{Institutional Factor}(s))$$

$$\text{e.g.,} = \lambda * FP_{source} + \eta * FP_{place} + \theta * NIH \text{ Funding}$$

where:

$FP_{source}=f(\text{Peers' Residency Program,Time Attended})$ $$\text{e.g.,} = \frac{1}{n}\sum_{i=0}^{n} C_i(\alpha RP, \mu S, \delta T)$$

where:
n=Number of physicians who attended the fellowship program
$C_i(\ )$=Individual physician's score
RP=Residency Program (e.g., Hospital for Special Surgery)
S=Specialty (e.g., General Surgery)
T=Time Attended (e.g., 1993)

$$\text{e.g.,} = \frac{1}{n}\sum_{i=0}^{n} RP_i$$

for all peers with the same specialty who attended the program within X years of the physician
where:
n=Number of physicians who attended the fellowship program
$RP_i$=A physician's Residency Program score $FP_{place}=f(\text{Peers' Practice Location,Time Attended})$ $$\text{e.g.,} = \frac{1}{n}\sum_{i=0}^{n} D_i(\alpha PL, \mu S, \delta T)$$

where:
n=Number of physicians who attended the fellowship program
$D_i(\ )$=Individual physician's score
PL=Practice Location/Group
S=Specialty (e.g., General Surgery)
T=Time Attended (e.g., 1993)

$$\text{e.g.,} = \frac{1}{n}\sum_{i=0}^{n} PL_i$$

for all peers with the same specialty who attended the program within X years of the physician
where:
n=Number of physicians who attended the fellowship program
PL=A physician's Practice Location/Group score In embodiments, the parameter weightings for any of the above-listed calculations (e.g., $\alpha$, $\mu$, $\delta$) may be determined programmatically. In embodiments, initial values may be assigned to all parameters. The weights may then be sequentially adjusted through iterations in order to minimize the mean difference between the quality rating for each step of a physician's training (med school, residency, fellowship training). In embodiments, as a default, the weights may be set to assign zero weight to all physicians who did not attend the same school and/or specialty as the physician and assign equal non-zero weight to all physicians who attended the same program, regardless of time attended. Determining a Physician's Overall Training Score Turning now to FIG. 6, depicted is a methodology for assigning an overall training score to a physician according to embodiments of the present invention. As shown in FIG. 6, an initial step is to initialize (605) values. For example, for the first iteration since Medical School (MS) scores are based upon Residency Program (RP) scores, which have not yet been calculated, the RP score may be set to an initial value or values. In addition, in embodiments, the initialization step may be considered to include compiling the initial raw data values, such as MCAT and GPA values, years and location of residency program(s), years and location of fellowship program(s), etc. This information may be stored in one or more storage devices and accessed by one or more processors.

Having gathered the raw data and initialized values, Medical School (MS) scores for a set of one or more physicians may be calculated (610) based upon attributes of medical students and Residency Program scores. In embodiments, the MS score may be calculated as discussed above in which MS=$f$(MS$_{source}$, MS$_{place}$, Institutional Factor(s)).

Having calculated the Medical School scores, Residency Program (RP) scores may be calculated (615) based upon the Medical School scores that were just calculated and Fellowship Programs scores. In embodiments, the RP score may be calculated as discussed above in which RP=$f$ (RP$_{source}$, RP$_{place}$, Institutional Factor(s)).

Having calculated the Residency Program scores, Fellowship Program (FP) scores may be calculated (620) based upon the Residency Program scores that were just calculated and Practice Location/Group scores. In embodiments, the FP score may be calculated as discussed above in which FP=$f$ (FP$_{source}$, FP$_{place}$, Institutional Factor(s)).

In embodiments, the process of assigning a physician's training score may be obtained by iterating the above steps until a stop condition has been reached. In embodiments, a stop condition may be considered to have been reached when a correlation (or correlations) between physicians' medical school, residency program, and fellowship quality scores is maximized Thus, in embodiments, one or more correlation factors may be calculated (625) using the MS, RP, and FP scores in order to determine if the process should stop or be iterated (630).

FIG. 7 depicts a methodology for determining a correlation factor as part of the iteration process according to embodiments of the present invention. In embodiments, for each iteration, two coefficients of determination are computed. A first coefficient of determination is calculated (705) where physicians' Residency Program scores are assumed to be a linear function of their Medical School scores. For example, in embodiments, the first coefficient of determination may be computed as follows:

$$R^2(RP, MS) = 1 - \frac{\sum_{i=0}^{n}(RP - MS)^2}{\sum_{i=0}^{n}(RP - \overline{RP})^2},$$

for all n physicians.

A second coefficient of determination is calculated (710) where physicians' Fellowship Program scores are assumed to be a linear function of their Residency Program scores. For example, in embodiments, the second coefficient of determination may be computed as follows:

$$R^2(FP, RP) = 1 - \frac{\sum_{i=0}^{n}(FP - RP)^2}{\sum_{i=0}^{n}(FP - \overline{FP})^2},$$

for all n physicians.

The coefficients may then be added together. In embodiments, greater weight may be placed on the correlation between residency and fellowship quality because residency performance is typically considered a better indicator of true quality than medical school performance. In embodiments, the coefficients may be combined together to form a correlation factor, $\sigma$, as follows:

$$\sigma = R^2(RP,MS) + \gamma \times R^2(FP,RP)$$

Thus, in embodiments, an objective of the iterative scoring is to maximize $\sigma$ across all physicians. When $\sigma$ is maximized, a stop condition is considered to be reached.

In embodiments, a number of stop conditions may be set. For example, a stop condition may be when a difference between the correlation factor for a current iteration and the correlation factor of a prior iteration is below a threshold. Another stop condition may be if the correlation factor starts to diverge (e.g., if the correlation factor for a current iteration is less than the correlation factor of a prior iteration). Also, a stop condition may be if a set number of iterations has been reached. One skilled in the art shall recognize that there are number ways of performing iterative calculations (including setting stop conditions), which may be employed herein.

It shall be noted that, in embodiments, in addition to iterating the training scoring process, the coefficients for each parameter may be modified. In embodiments, an objective is to set the optimal weightings so that the scoring iterations achieve the absolute minimum solution, rather than a local minimum.

In embodiments, to achieve optimal weightings, the process is started with a simple set of weights, which are then systematically experimented with by altering these values. Consider, by way of illustration, the following example methodology:

Step #1—set the initial coefficients:
  $\alpha$, the coefficient for program quality (MS, RP, FP) may be set to 1 for all programs;
  $\mu$ and $\delta$, the coefficients for specialty, S, and time attended, T, may be set to 0 for all physicians;
  $\lambda$ and $\eta$, the coefficients for programs' sourcing and placement quality, may be set to 0.5 for all programs; and
  $\theta$, the coefficient for NIH funding (or some other institutional factor or factors), may be set to 0.

Step #2—adjust the specialty coefficients. In embodiments, $\mu$ may be incrementally increased until $\sigma$ no longer decreases with each increase; this may be done for one or more specialty at a time to account for the fact that the optimal coefficient may vary by specialty.

Step #3—adjust the time attended coefficients. In embodiments, $\delta$ may be incrementally increased until $\delta$ no longer decreases with each increase; this may be done for one or more specialty at a time to account for the fact that the optimal coefficient may vary by specialty.

Step #4—adjust other institutional factor coefficients. In embodiments, $\theta$ may be increased incrementally until $\delta$ no longer decreases with each increase; this too may be done for one or more specialty at a time to account for the fact that the optimal coefficient may vary by specialty.

In embodiments, the physician's training programs may be scored iteratively with different combinations of parameter coefficients until an absolute minimum for 6 is achieved.

Figure 8:
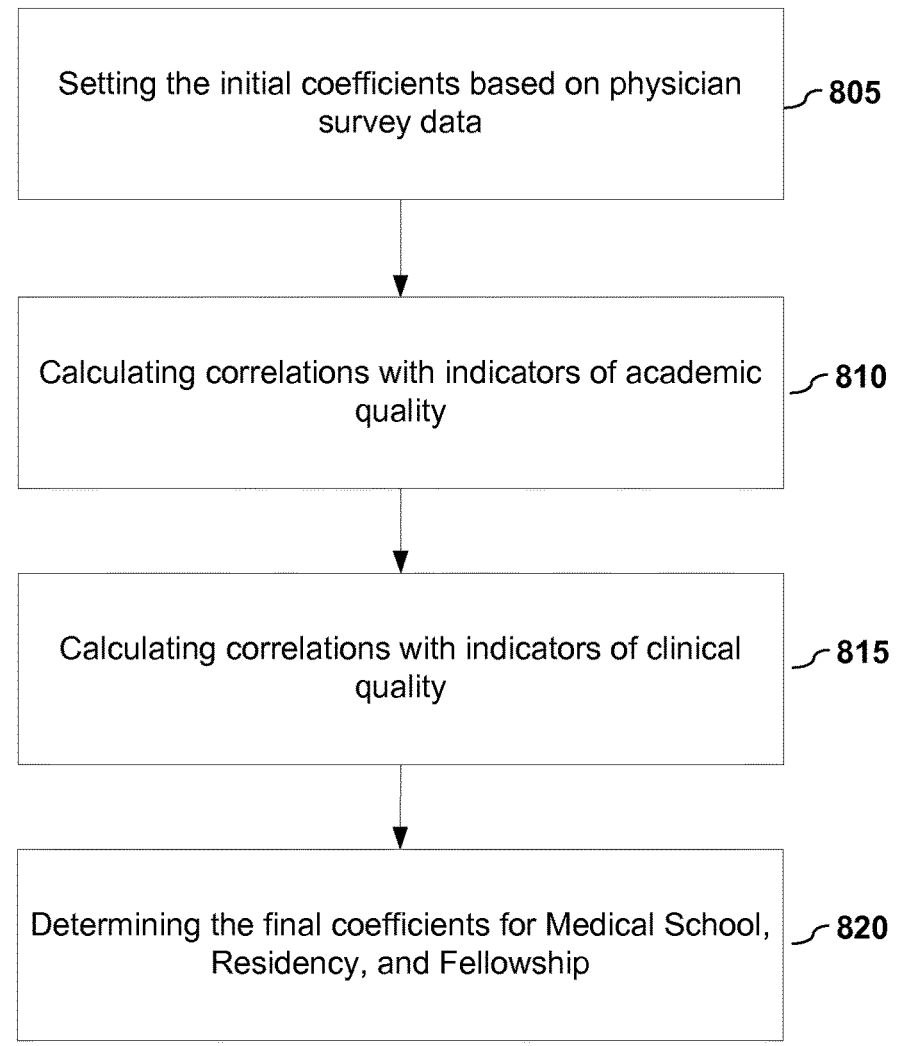
FIG. 8 depicts a method for assigning a physician's overall training using correlations according to embodiments of the present invention.

Returning to FIG. 6, once a stop condition has been reached (630), in embodiments, a physician's overall training score may be computed using the physician's final Medical School, Residency Program, and Fellowship Program scores. In embodiments, a composite quality score of a physician's training may be determined as follows:

$$MD_{train} = \text{Composite training quality score}$$
$$= f(MS, RP, FP)$$
$$= \alpha MS + \mu RP + \delta FP$$

where:
MS=Medical School score
RP=Residency Program score
FP=Fellowship Program score In embodiments, the coefficients for medical school, residency, and fellowship scores may be calibrated against other external indicators of physician quality. FIG. 8 depicts a method for assigning a physician's overall training using correlations according to embodiments of the present invention.

In embodiments, the initial coefficients may be based (805) on physician survey data. Typically, physicians place the greatest weight on their peer's fellowship training, the second greatest weight on residency training, and the least weight on medical school attended. Thus, in embodiments, to approximate these preferences, the coefficients may be set as follows: $\alpha=0.2$; $\mu=0.35$; and $\delta=0.45$—although it shall be noted that other values may be set.

Then, in embodiments, correlations may be calculated (810) with indicators of academic quality. At academic centers, two indicators of physician quality are: (1) positions held, and (2) publication track record. Academic physicians may be first rated based on the number of positions held with certain titles (e.g., chief, head, or director). They may also be rated based on volume and quality of publications, as measured by the impact factor of the publishing journal $$(\text{e.g.,} \sum_{i=0}^{n} J_i,$$

where n=number of publications, J=journal's impact factor).

In embodiments, the coefficients of determination, $R^2$, for each training variable and measure of academic quality may then be calculated:

TABLE A

|  | Medical School Score | Residency Program Score | Fellowship Program Score |
|---|---|---|---|
| Positions Held Score | $R^2_{MS, PH}$ | $R^2_{RP, PH}$ | $R^2_{FP, PH}$ |
| Publication Score | $R^2_{MS, P}$ | $R^2_{RP, P}$ | $R^2_{FP, P}$ |

In embodiments, the correlations with indicators of clinical quality are also calculated (815). Clinical quality may be ascertained from physician's outcomes data (e.g., mortality rates, readmission rates, complication rates, etc.), peer opinion, and preferred clinical practices, among other factors. In embodiments, to calibrate the training quality measures, specialties in which outcomes data and peer opinion are likely to be accurate indicators of true clinical quality may be focused upon. Such specialties may include cardiothoracic surgery, cardiology, oncology, neurosurgery, and orthopedic surgery. Outcomes data may be based on published indicators of physician performance. For example, what percent of patients are readmitted to the hospital within 30 days of receiving a knee replacement from a given orthopedic surgeon?

In embodiments, peer opinion may be obtained by surveying physicians about their peers in the same specialty and geographic region (e.g., other thoracic surgeons in the same state). Physicians may be asked to identify which of their peers they would recommend to patients if they, themselves, were unable to see the patient or who they would select as their doctor.

In embodiments, preferred clinical practices may be inferred from provider-level claims data. This analysis may focus on specific procedures or treatments where many physicians are not treating patients according to the latest recommended guidelines. For example, the best urologists treating renal cell carcinoma will conduct three partial nephrectomies for every full nephrectomy; however, many urologists still default to the old standard of conducting full nephrectomies in a majority of patients.

In embodiments, coefficients of determination, $R^2$, may then calculated for each training variable and each clinical performance measure:

TABLE B

|  | Medical School Score | Residency Program Score | Fellowship Program Score |
|---|---|---|---|
| Outcomes Data Score | $R^2_{MS, O}$ | $R^2_{RP, O}$ | $R^2_{FP, O}$ |
| Peer Opinion Score | $R^2_{MS, PO}$ | $R^2_{RP, PO}$ | $R^2_{FP, PO}$ |
| Clinic Practice Score | $R^2_{MS, CP}$ | $R^2_{RP, CP}$ | $R^2_{FP, CP}$ |

Given the various coefficients, final coefficients may be determined (820). In embodiments, an average of the coefficients of determination may be used to calculate the final coefficients for medical school, residency, and fellowship. Note that the academic quality indicators are only included for physicians who practice at academic institutions.

TABLE C

|  | Medical School Score | Residency Program Score | Fellowship Program Score |
|---|---|---|---|
| Positions Held Score | $R^2_{MS, PH}$ | $R^2_{RP, PH}$ | $R^2_{FP, PH}$ |
| Publication Score | $R^2_{MS, P}$ | $R^2_{RP, P}$ | $R^2_{FP, P}$ |
| Outcomes Data Score | $R^2_{MS, O}$ | $R^2_{RP, O}$ | $R^2_{FP, O}$ |
| Peer Opinion Score | $R^2_{MS, PO}$ | $R^2_{RP, PO}$ | $R^2_{FP, PO}$ |
| Clinic Practice Score | $R^2_{MS, CP}$ | $R^2_{RP, CP}$ | $R^2_{FP, CP}$ |

For example, in embodiments, a, the coefficient for medical school may be set to equal:

For academics: $\alpha=(R^2_{MS,P}+R^2_{MS,P}+R^2_{MS,P}+R^2_{MS,P}+R^2_{MS,P})/[\text{Sum of all } R^2]$ For non-academics: $\alpha=(R^2_{MS,P}+R^2_{MS,P}+R^2_{MS,P})/[\text{Sum of all clinical } R^2]$ It shall be noted that, in embodiments, the denominator equals the sum of all $R^2$ for medical school, residency, and fellowship scores. It shall also be noted that, in embodiments, additional coefficients may be added to this equation to place greater weight on certain clinical or quality indicators. The example above reflects a straight average that assigns equal weight to each indicator.

6. Rating the Physician's Past and Current Practice Groups/Locations

In embodiments, quality of a physician's post-training practice groups/locations (P) may be determined by the quality of their peers at each practice. It shall be noted that practice location may mean practice group (including doctors who work in a small group, in the same department, in the same team, etc.), physicians working for the same organization (e.g., physicians in the same department, in the same hospital, in the same organization, etc.), even if the physicians are not at the same physical location.

Figure 9:
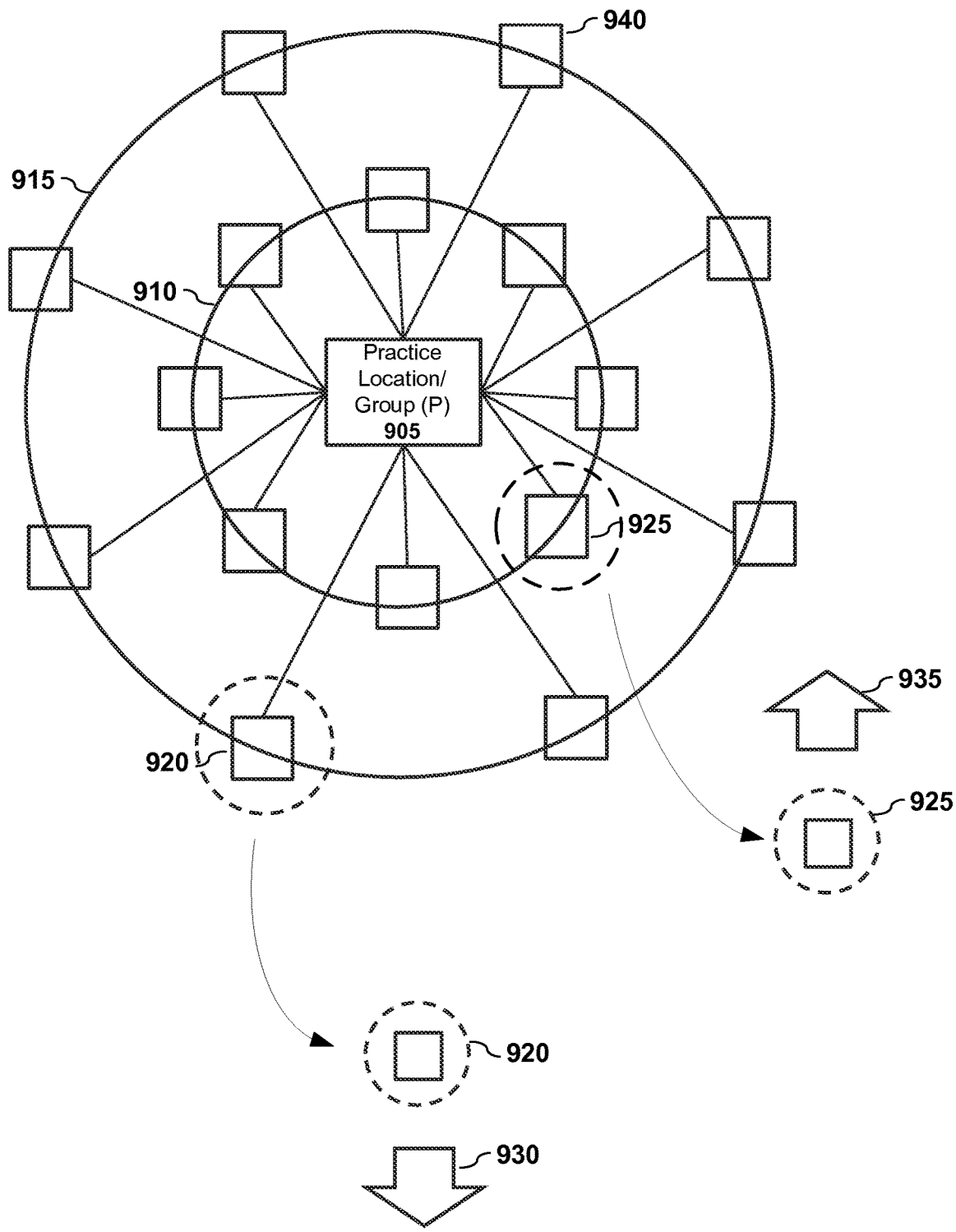
FIG. 9 graphically depicts the relationships between peers and practice locations/groups according to embodiments of the present invention.

FIG. 9 graphically depicts the relationships between peers and practice locations/groups according to embodiments of the present invention. In embodiments, a practice location 905 of a physician may be represented as having a set of one or more peers (e.g., box 940 may represent a single peer or a group of peers).

In embodiments, peer quality may be determined by the quality of physicians' overall training. In alternative embodiments, peer quality may also be a function of one or more additional factors, such as (by way of example and not limitation), publications, outcomes data, honors & awards, positions held, and the patient referrals they receive from other physicians.

In embodiments, each peer set may be weighted by "proximity" to the physician of interest. FIG. 9 graphically depicts these "proximity" connections via the circles or rings. For example, the inner circle 910 represents physicians who work in the same department and at the same time as the selected physician. And, in embodiments, the outer circle 915 represents peer groups that were in the same department but at a different time period or that were in different programs at the same institution. Only two groups 910 and 915 are depicted for sake of explanation, but it shall be noted that more or fewer groups may be considered and that the categories may represent various factors or various combinations of factors.

In embodiments, a practice group or location score quality may be weighted by peer's "proximity," as determined by one or more nexus factors, such as (by way of example and not limitation), when they worked at the practice location, whether they worked for the same department or a related department, and how much time they spent at that practice location. In embodiments, disproportionate weight may be assigned to the top physicians at each practice location.

As shown in FIG. 9, in embodiments, physicians who have a close nexus to the selected physician (e.g., peer set 925) may have a higher proximity weighting as depicted by the weighting factor 935. Conversely, in embodiments, physicians (e.g., physician set 920) who do not have as close a nexus to the selected physician may be given less weight as graphically illustrated by the weighting factor 930.

In embodiments, the Practice Group/Location (P) score may be determined as follows:

$P$ = Practice Location/Group Score
(e.g., SF General Hospital, Cardiology, 2014)
= $f$(Peers' Quality, Proximity)

$$\text{e.g.} = \frac{\sum_{i=1}^{n} MD_{train_i} * \left(\frac{1}{1+\mu i}\right) * D_i(Dept, \text{Years})}{\sum_{i=1}^{n} \left(\frac{1}{1+\mu i}\right) * D_i(Dept, \text{Years})}$$

where:
n=Number of physicians who have worked at the practice location (e.g., SF General Hospital)
$MD_{train}$=Quality of physician's training program
$D_i( )$=Proximity of the physician to the practice group
  e.g., $D_i( )$=1 if same department and practiced there at the same time
  $D_i( )$=0 if different department or practiced there at different time In embodiments, physicians at each practice group are ranked in descending order by training quality score so that the greatest weight is placed on the top physicians at the practice.

In embodiments, μ may be calibrated based on peer ratings of top academic institutions around the country. An academic experts panel may be asked to identify the top 5 institutions for their medical specialty. μ may then be adjusted to maximize the $R^2$ between the algorithm's ratings of the top 10 academic institutions in each specialty and the number of votes received from the panelists.

7. Determining A Physician's Overall Quality Score

FIG. 10 depicts a method for determining a physician's overall quality score according to embodiments of the present invention. As depicted, a physician's training score, which may be based, at least in part, upon quality of the physician's peers, is determined (1005). This training score may be determined as described above.

Also, in embodiments, a rating for the physician's practice group/location, which may be based, at least in part, upon quality of the physician's peers at the practice group/location, is determined (1010). This score may be determined as described above.

Given a physician's training score and a physician's practice score, the physician's overall quality score may be assigned (1015) to the physician based, at least in part, upon those values. In embodiments, the overall quality score of a physician may be calculated as a weighted average of the physician's training quality score and the average quality score of their practice groups.

$$MD_{quality} = \alpha MD_{train} + \mu \overline{P}$$

where $\mu \overline{P}$=mean quality score of a physician's practice groups/locations In embodiments, as a default, equal weight may be assigned to both coefficients, a and μ. In alternative embodiments, disproportional weight may be placed on the highest scoring practice groups a physician is affiliated with.

8. Using a Physicians' Scoring

Having assigned a physician's overall quality score, this information may be used in various ways. For example, in embodiments, a patient may use this information to help identify a physician.

In embodiments, a patient may use this information to help identify which physician is the best "fit" for him or her to provide care. In embodiments, "fit" may be determined not only by the physician's overall quality score but may also be based on, or weighted against, various factors including, but not limited to, the physician's specific area of sub-specialty training, stated clinical interests, volume of clinical experience, distance from the patient, appointment availability, and past patient satisfaction scores. One skilled in the art shall recognize that other factors, weights, and matching methods may be employed to align a patient with the best qualified doctor.

9. Computing System Embodiments

Figure 11:
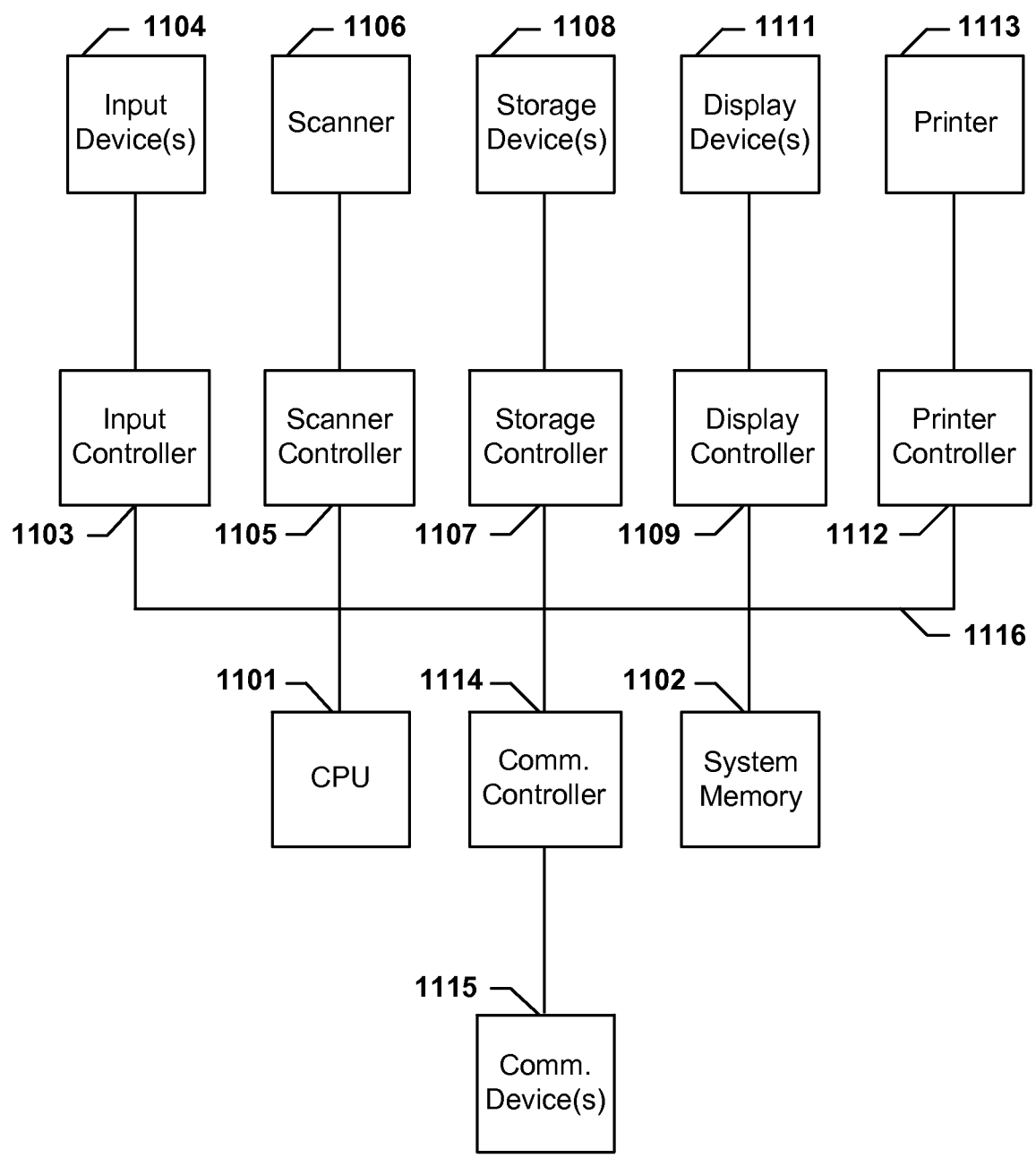
FIG. 11 depicts a block diagram of an exemplary information handling system node according to embodiments of the present invention.

Having described the details of the invention, an exemplary system 1100, which may be used to implement one or more of the methodologies of the present invention, will now be described with reference to FIG. 11. As illustrated in FIG. 11, the system includes a central processing unit (CPU) 1101 that provides computing resources and controls the computer. The CPU 1101 may be implemented with a microprocessor or the like, and may also include a graphics processor and/or a floating point coprocessor for mathematical computations. The system 1100 may also include system memory 1102, which may be in the form of random-access memory (RAM) and read-only memory (ROM).

Figure 12:
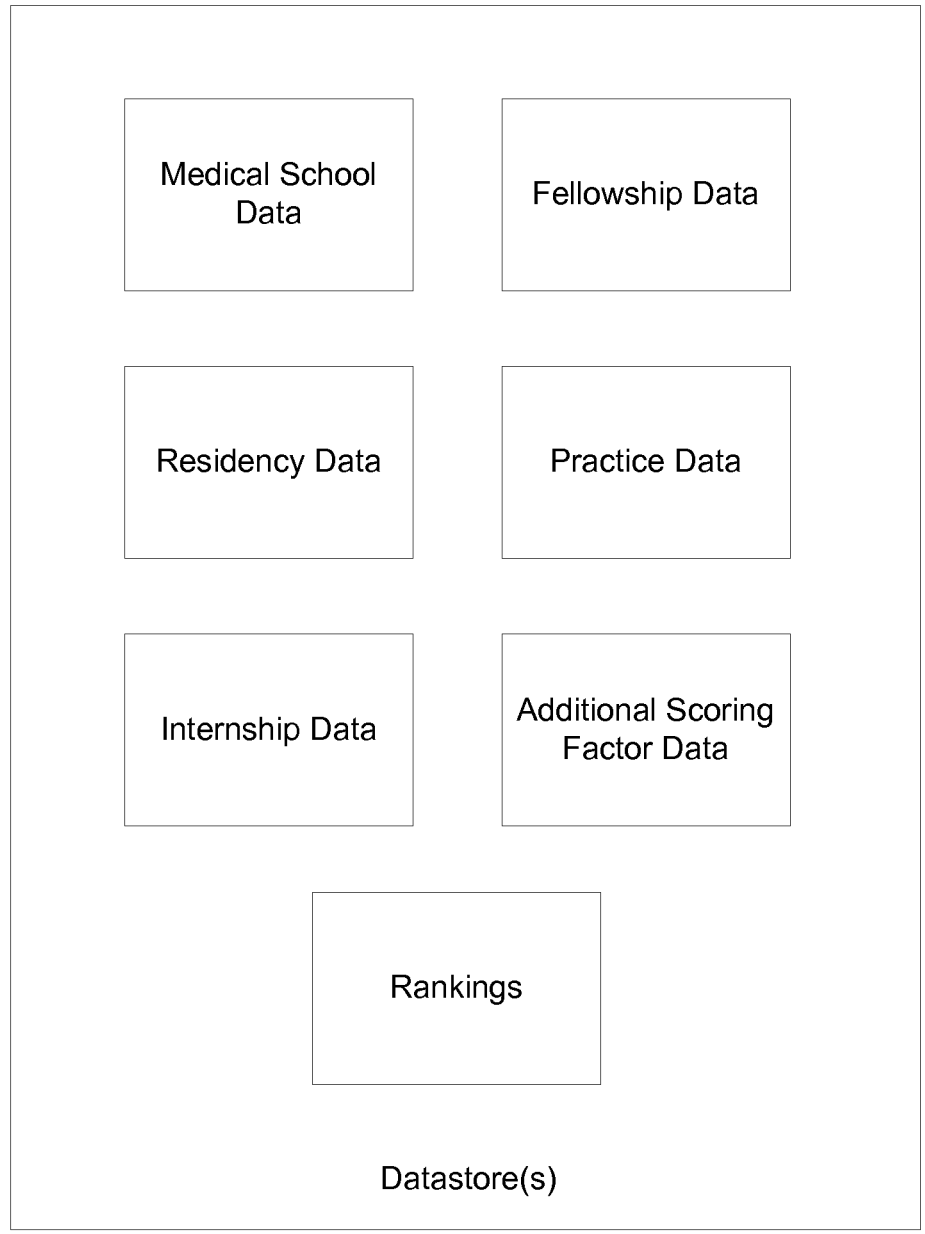
FIG. 12 depicts a block diagram of one or more sets of datastores according to embodiments of the present invention.

A number of controllers and peripheral devices may also be provided, as shown in FIG. 11. An input controller 1103 represents an interface to various input device(s) 1104, such as a keyboard, mouse, or stylus. There may also be a scanner controller 1105, which communicates with a scanner 1106. The system 1100 may also include a storage controller 1107 for interfacing with one or more storage devices 1108 each of which includes a storage medium such as solid state drives, magnetic tape or disk, or an optical medium that might be used to record programs of instructions for operating systems, utilities and applications which may include embodiments of programs that implement various aspects of the present invention. Storage device(s) 1108 may also be used to store processed data or data to be processed in accordance with the invention, including data for determining a physician's score(s). FIG. 12 depicts at least some datastores that may be used in assessing a physicians' score(s) or ranking(s) according to embodiments of the present invention. The system 1100 may also include a display controller 1109 for providing an interface to a display device 1111, which may be a cathode ray tube (CRT), a thin film transistor (TFT) display, or other type of display. The system 1100 may also include a printer controller 1112 for communicating with a printer 1113. A communications controller 1114 may interface with one or more communication devices 1115, which enables the system 1100 to connect to remote devices through any of a variety of networks including the Internet, a local area network (LAN), a wide area network (WAN), or through any suitable electromagnetic carrier signals including infrared signals.

In the illustrated system, all major system components may connect to a bus 1116, which may represent more than one physical bus. However, various system components may or may not be in physical proximity to one another. For example, input data and/or output data may be remotely transmitted from one physical location to another. In addition, programs that implement various aspects of this invention may be accessed from a remote location (e.g., a server) over a network. Such data and/or programs may be conveyed through any of a variety of machine-readable medium including magnetic tape or disk or optical disc, or a transmitter, receiver pair.

Embodiments of the present invention may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to write program code (i.e., software) and/or to fabricate circuits (i.e., hardware) to perform the processing required.

While the inventions have been described in conjunction with several specific embodiments, it is evident to those skilled in the art that many further alternatives, modifications, application, and variations will be apparent in light of the foregoing description. Thus, the inventions described herein are intended to embrace all such alternatives, modifications, applications and variations as may fall within the spirit and scope of the appended claims.

What is claimed is:

1. The quality scoring system comprising:
a memory;
one or more processors configured to cause the quality scoring system to:
obtain, from one or more data sources, one or more data sets associated with a plurality of individuals;
determine a first set of training values of a plurality of training values associated with an individual of the plurality of individuals, wherein the first set of training values are based on a seed value related to the individual's training and are iteratively determined using a series of correlation factors based on a plurality of training values that are prior iterations of the first set of training values and a condition evaluated on the series of correlation factors, wherein determination of first set of training values of the individual comprises:
determining each correlation factor of the series of correlation factors using first and second coefficients that are each associated with a plurality of different types of training values; and
applying the series of correlation factors to training values of the plurality of individuals;
determine a practice location value associated with the individual based on practice-location attributes of at least some of the plurality of individuals; and
determine a quality score of the individual using the practice location value and the first set of training values.

2. The quality scoring system of claim 1, wherein the first coefficient is determined using a first type of training value and a second type of training value.

3. The quality scoring system of claim 2, wherein the second coefficient is determined using the second type of training value and a third type of training value.

4. The quality scoring system of claim 1, wherein the first set of training values are determined based on a modification of the first and second coefficients.

5. The quality scoring system of claim 1, wherein the first and second coefficients are averaged to determine final coefficients that are used to determine the first set of training values.

6. The quality scoring system of claim 1, wherein the condition evaluated on the series of correlation factors is difference between a present correlation factor of the series of correlation factors and a prior correlation factor of the series of correlation factors is below a threshold.

7. The quality scoring system of claim 1, wherein the condition evaluated on the series of correlation factors is whether a present correlation factor of the series of correlation factors is less than a prior correlation factor of the series of correlation factors.

8. The quality scoring system of claim 1, wherein the condition evaluated on the series of correlation factors is completion of a predetermined number of iterations.

9. The quality scoring system of claim 1, wherein the training values include a first type of training value, a second type of training value, and third type of training value;
- wherein the first type of training value is determined using attributes of the at least some of the plurality of individuals and a second type of training value,
- the second type of training value is determined using attributes of the at least some of the plurality of individuals and the first type of training value and a third type of training value, and
- the third type of training value is determined using attributes of the at least some of the plurality of individuals and the second type of training value and the practice location value.

10. The quality scoring system of claim 9, wherein the first type of training value is a medical school score, the second type of training value is a residency program score, and the third type of training value is a fellowship program score.

11. The quality scoring system of claim 1, wherein the set of instructions that is executable by the computing device to cause the computing device to perform:
- displaying, to a user, information based on the determined quality score of the individual.

12. The quality scoring system of claim 11, wherein the displayed information is based on a request for information about the individual.

13. A method performed by a quality scoring system for calculating quality score of an individual, the method comprising:
- obtaining, from one or more data sources, one or more data sets associated with a plurality of individuals;
- determining a first set of training values of a plurality of training values associated with an individual of the plurality of individuals, wherein the first set of training values are based on a seed value related to the individual's training and are iteratively determined using a series of correlation factors based on a plurality of training values that are prior iterations of the first set of training values and a condition evaluated on the series of correlation factors, wherein determination of first set of training values of the individual comprises:
  - determining each correlation factor of the series of correlation factors using first and second coefficients that are each associated with a plurality of different types of training values; and
  - applying the series of correlation factors to training values of the plurality of individuals;
- determining a practice location value associated with the individual based on practice-location attributes of at least some of the plurality of individuals; and
- determining a quality score of the individual using the practice location value and the first set of training values.

14. The method of claim 13, wherein the first coefficient is determined using a first type of training value and a second type of training value.

15. The method of claim 14, wherein the second coefficient is determined using the second type of training value and a third type of training value.

16. The method of claim 13, wherein the first set of training values are determined based on a modification of the first and second coefficients.

17. The method of claim 13, wherein the condition evaluated on the series of correlation factors is difference between a present correlation factor of the series of correlation factors and a prior correlation factor of the series of correlation factors is below a threshold.

18. The method of claim 13, wherein the condition evaluated on the series of correlation factors is whether a present correlation factor of the series of correlation factors is less than a prior correlation factor of the series of correlation factors.

19. The method of claim 13, wherein the training values include a first type of training value, a second type of training value, and third type of training value;
- wherein the first type of training value is determined using attributes of the at least some of the plurality of individuals and a second type of training value,
- the second type of training value is determined using attributes of the at least some of the plurality of individuals and the first type of training value and a third type of training value, and
- the third type of training value is determined using attributes of the at least some of the plurality of individuals and the second type of training value and the practice location value.

20. The method of claim 13, wherein the set of instructions that is executable by the computing device to cause the computing device to perform:
- displaying, to a user, information based on the determined quality score of the individual.

* * * * *